United States Patent [19]

Gehrman et al.

[11] Patent Number: 4,518,696
[45] Date of Patent: May 21, 1985

[54] STABILIZED LIQUID BACTERIAL SUSPENSION FOR ORAL ADMINISTRATION TO ANIMALS

[75] Inventors: Sybil H. Gehrman; Randolph S. Porubcan, both of West Allis, Wis.

[73] Assignee: Chr. Hansen's Laboratory, Inc., Milwaukee, Wis.

[21] Appl. No.: 457,226

[22] Filed: Jan. 11, 1983

[51] Int. Cl.³ .................... C12N 1/20; C12N 1/04; C12R 1/225; C12R 1/23
[52] U.S. Cl. .................................. 435/253; 435/260; 435/853; 435/854; 426/61; 426/807; 424/93
[58] Field of Search ............... 435/253, 260, 853, 854, 435/245; 424/93; 426/61, 807

[56] References Cited

U.S. PATENT DOCUMENTS

| | | | |
|---|---|---|---|
| 1,758,937 | 5/1930 | Earp-Thomas | 435/253 X |
| 3,034,968 | 5/1962 | Johnston | 435/253 X |
| 3,420,742 | 1/1969 | Farr | 435/253 |
| 3,897,307 | 7/1975 | Porubcan et al. | 435/253 X |
| 4,161,397 | 7/1979 | Bellet et al. | 435/260 X |

OTHER PUBLICATIONS

Pivnyak et al, Abstract of "Effect of Feeding With Carotene-Forming Microflora Obtained From the Digestive Tract on Vitamin A Requirement of Chickens", *Commonwealth Agricultural Bureaux Abstracts*, Abstract No. 539154; 1973.

*Chemical Abstracts*, vol. 94, 1981, Abstract No. 49562, Stewart, "Extraction Process Using Stabilized Emulsions".

*Primary Examiner*—Sidney Marantz
*Assistant Examiner*—Randall E. Deck

[57] ABSTRACT

Stabilized liquid suspensions of probiotic Lactobacilli are provided as a dispersion of the viable cells in sunflower seed oil for administration to animals. The viable cells prior to combining with the oil have been dried at a favorable pH and in the presence of stabilizing additives. The dried cells are further characterized by having a low water activity. The invention has particular utility in administering *Lactobacillus acidophilus* cells as a drench to domestic animals.

4 Claims, No Drawings

STABILIZED LIQUID BACTERIAL SUSPENSION FOR ORAL ADMINISTRATION TO ANIMALS

BACKGROUND AND PRIOR ART

The field of this invention relates to the stabilization of dried bacterial cells, especially Lactobacilli. The kind of stabilization involved is of such a nature as to permit non-refrigerated, room temperature storage of the bacterial cells while maintaining a high percentage of viability over storage periods of weeks or months. In preferred embodiments, the invention relates to stabilized probiotic Lactobacilli for administration to domestic animals such as chickens, turkeys, swine, cattle, sheep, etc., and/or to small animal pets such as dogs, cats, etc. In fact, the stabilized bacterial suspensions of the present invention are believed useful for administration to a wide variety of birds and mammals.

While many Lactobacilli are potentially useful for probiotic administration, the most widely used lactobacillus for this purpose is *L. acidophilus*. Dried stabilized concentrates of *L. acidophilus* have been administered to mammals in milk and other aqueous suspensions. Unless the suspension is to be stored and distributed under refrigerated conditions, such as with commercial acidophilus milk, it has heretofore been necessary to prepare the suspension immediately prior to use in order to be certain that a sufficiently high percentage of the cells administered remain viable at the time of administration.

Lactobacillus cell concentrates can be prepared as described in Porubcan and Sellars U.S. Pat. No. 4,115,199, and these cell concentrates can be dried to obtain stabilized dry cultures as described in Porubcan and Sellars U.S. Pat. No. 3,897,307. Such dried cell concentrates maintain a high percentage of viable cells with room temperature storage and handling. However, the cells are not adequately stable in aqueous suspension unless the suspension is refrigerated. Therefore, in using such stabilized dry cultures in the form of a liquid drench for administration to domestic animals, the cells have been packaged and distributed as a two-part formulation, the dry cell concentrate being packaged separately from the dry suspending agents, both of which must be reconstituted in water prior to use.

There has been a need for a more convenient drench-type product in which the Lactobacillus cells are prepared in a liquid suspension which can be stored and distributed without serious loss of the viability of the cells. The present invention for the first time, as far as is known, provides a means for preparing products meeting this need.

SUMMARY OF INVENTION

This invention is based in part on the discovery that sunflower seed oil, when used as the liquid suspending medium for properly prepared dry viable Lactobacillus cells, results in a cell suspension manifesting a high degree of cell stability at room temperature. While other highly unsaturated vegetable oils also tend to somewhat promote the stability of the Lactobacillus cells, sunflower seed oil appears to have unique properties in this respect. Further, the cells can be maintained in suspension in the oil by incorporating a small amount of fumed silica. By utilizing the sunflower seed oil medium together with the conditions and additives known to improve the stability of dry Lactobacilli, long term room temperature stability can be obtained. In optimizing the stability, it has also been found important to test the dry cells for water activity, and to utilize cells having a water activity below 0.2, such as about 0.05 to 0.10 $a_w$.

DETAILED DESCRIPTION

The method and resulting products of this invention are generally applicable to preparing liquid bacterial suspensions from harmless lactic acid-producing bacteria cells. Species of Lactobacillus are particularly suitable, including *L. acidophilus*, *L. plantarum*, *L. lactis*, *L. bifidus*, *L. bulgaricus*, *L. helveticus*, and *L. casei*. Some or all of these bacteria are potentially useful for probiotic administration to domestic animals and animal pets. The presently preferred Lactobacillus for probiotic purposes is *L. acidophilus*. This species will therefore be particularly referred to in the following exemplification of the present invention, but it should be understood that the invention is not limited thereto.

For use in preparing the liquid suspension, the Lactobacilli or other lactic-acid producing species are first prepared in the form of concentrates, which are then converted to a dry stabilized form. The preferred concentration procedure is the one described in Porubcan and Sellars U.S. Pat. No. 4,115,199, which utilizes a polyphosphate salt, such as sodium hexametaphosphate or sodium tripolyphosphate as an additive to the culture medium prior to concentration by centrifugation. With this procedure, cell concentrates can be obtained ranging from 50 to $200 \times 10^9$ CFU per gram. The wet cell concentrates are then preferably dried under stabilizing conditions and in the presence of stabilizing additives as described in Porubcan and Sellars U.S. Pat. No. 3,897,307. More specifically, the cell concentrate is adjusted to a pH favorable to cell stability, such as a pH in the range from 5.8 to 7.0. The preferred pH is from about 6.0 to 6.5, such as a pH of 6.2. Stabilizing additives are dissolved in the aqueous medium of the wet cells prior to drying.

As described in U.S. Pat. No. 3,897,307 the additives used as stabilization potentiators should include an ascorbate compound such as L-ascorbic acid or the water soluble salts thereof, such as sodium ascorbate, and also a second potentiator selected from glutamic acid, or aspartic acid, or the edible water-soluble salts thereof. The amounts to be used of the ascorbate compound is the amount equivalent on a molar basis to 4 to 20 parts by weight L-ascorbic acid, and for the second potentiator the amount equivalent on a molar basis to 1.5 to 20 parts by weight of monosodium glutamate per each 100 parts of the dried cells mass. The cells are dried by a suitable drying procedure such as freeze drying. Spray drying may also be used, but a larger loss of viability may occur in the spray drying process as compared with freeze drying. The procedure can produce dried cell concentrates of 80 to $150 \times 10^9$ CFU per gram. The term "CFU" as used herein refers to the determination of colony forming units by standard bacteriological plating procedures.

Commercial grade sunflower seed oil can be used as the liquid medium. It is preferably the only liquid ingredient of the medium. Commercial sunflower seed oil has been processed from the raw oil, and is supplied commercially as refined, bleached, and deodorized oil. Typically sunflower seed oil has an iodine value of about 125–136, a saponification value of about 188–194, and has a high content of linoleic acid, such as 44 to 75% of the fatty acids of the triglycerides. Commercial sunflower seed oil is substantially anhydrous.

The dried stabilized cell concentrate need not be totally moisture free, but can contain some internal moisture, such as about 2% to 8% moisture. But a low moisture content is desirable. The critical factor is believed to be best expressed in terms of water activity ($a_w$). The $a_w$ of the dried cells as determined by standard test procedure should be below 0.20 and preferably below 0.10, such as a water activity in the range of 0.05–0.10. A suitable instrument for determining water activity is available from Kaymont Instrument, Huntington Station, N.Y., or from Rotronic Ag, Zurich, Switzerland.

The desirable mixing procedure for preparing the liquid suspension products is easy to carry out. The sunflower seed oil, which may be chilled to compensate for heat generated in the subsequent mixing, is introduced into a high speed mixer, and the cell concentrate is added in an amount to produce the desired final cell count in the liquid suspension. While the concentration can vary over a considerable range, the preferred concentrations can range from about $1 \times 10^8$ to $1 \times 10^{10}$ (CFU) per cubic centimeter (cc) of oil. In certain preferred embodiments, such as in preparing a liquid suspension product from *L. acidophilus*, the desired cell suspension may be in the range from about $1 \times 10^9$ to $1 \times 10^{10}$ CFU per cc of the oil-cell mixture.

After a thorough dispersion of the cells in the oil, a suspending agent can be added such as fumed silica. This material is produced by flame hydrolysis of silicon tetrachloride. It can be obtained from various manufacturers, including the Cab-O-Sil products of Cabot Corporation, Boston, Mass., and the Aerosil Products of Degussa, Inc., New York, N.Y. These products are colloidal silicon dioxide of very high surface area, which are supplied as dry white powders. For example, one particularly suitable product for the purpose of the present invention is "Cab-O-Sil PTG". This grade of Cab-O-Sil permits formation of the suspension with minimal shear, which reduces the required mixing and resulting heating of the mixture. But fumed silica is in general a suitable suspending agent. An effective amount of the fumed silica will be used to obtain the suspension, usually somewhat less than 3.0% based on the weight of the oil-cell mixture. A suitable range is usually from about 0.5 to 2.0% fumed silica based on the weight of the oil-cell mixture, such as around 1.5%. In adding the fumed silica, it is preferred to control the temperature of the mixture to below 35° C., such as a maximum temperature of 28° to 30° C.

With the introduction of the fumed silica, a suspension is obtained having a high degree of cell stability. The suspension can be stored, distributed, and used at room temperature without serious loss of cell viability for several weeks or months. Further, the suspension exhibits minimal settling, so that the cells remain in suspension. If some settling occurs, on long standing, the portion of settled cells can easily be resuspended by mild shaking. This permits the complete product to be packaged in a single container for convenient distribution and use as a drench for oral administration to domestic animals.

This invention is further illustrated by the following examples.

EXAMPLE I

A stabilized dry cell concentrate of *L. acidophilus* is prepared according to the procedures described in U.S. Pat. Nos. 4,115,199 and 3,897,307. The strain of *L. acidophilus* used, designated LA-1, has been deposited with the Northern Regional Research Center, USDA, Peoria, Ill., and is publicly available as Strain NRRL No. B-15260. The cell concentrate is dried by freeze drying after adjusting the pH to 6.0–6.2, and the addition of 16 grams of L-ascorbic acid and 10 grams of monosodium glutamate per 100 grams of the cell mass (dry basis). The resulting stabilized dry concentrate provides around $100 \times 10^9$ CFU per gram.

The presently preferred procedure for preparing the liquid suspension product is as follows:

(1) 840 pounds sunflower seed oil (refined, bleached, deodorized), is used as the oil medium. The oil is preferably maintained at low temperatures (10°–15° C.) to compensate for heat generated in the mixing.

(2) The sunflower seed oil is added to a high speed, bottom-driven mixer. The dried stabilized concentrate of the *L. acidophilus* (Strain LA-1) is added to the oil in amounts needed to meet desired colony forming units (CFU) count. For example, in the case of a drench product with a blend strength of $4 \times 10^9$ CFU/ml, it is necessary to add 36.67 pounds or approximately 37 pounds of freeze-dried LA-1 at strength $100 \times 10^9$ to 840 pounds of sunflower seed oil. This culture/oil mixture is blended for about 1.0–2.0 minutes at low speed (800 RPM) in the mixer.

(3) After the culture is dispersed in the sunflower seed oil, fumed silica (CAB-O-SIL PTG) is slowly added (over 5 minutes of mixing time) to the mixture under low speed mixing at a rate of 1.0–1.5% by weight. For 840 pounds of oil and 37 pounds of 100 strength powder, 8.8–13.2 pounds of fumed silica are added.

(4) When all the fumed silica has been added to the culture/oil mixture, the speed is increased to the high setting (1900 RPM) and mixing continues for 15–18 minutes at 3 minute intervals. At the intervals, the temperature is measured, and should not exceed 35° C. maximum, with temperatures in the 28°–30° C. maximum being preferred.

(5) The final product can be pumped into 55 gallon drums for later repackaging in small containers.

EXAMPLE II

The stabilization effectiveness of sunflower oil was compared with other vegetable oils, including cottonseed oil and corn oil. Test samples were prepared by weighing out 200 g of each oil and adding 1 g of the LA-1 freeze-dried cell concentrate (*L. acidophilus*) described in Example I. Samples were placed in sterile flasks and stirred magnetically for 5 minutes. Platings were done on Lactobacilli MRS Agar (Difco Laboratories, Detroit, Mich.) in triplicate, and incubated at 37° C. for 3 days.

The following plating procedure was used:

(1) Initial dilution of 1:100 was prepared and shaken 80–100 times.

(2) Initial dilution was then allowed to rest 5 minutes.

(3) Proceeded as usual with remaining dilutions.

Plating intervals were at 0, 9, 70 and 120 days. LA-1 powder and oil controls were also plated on 0 day. Samples were stored at 23° C. between platings.

The results of the comparison are summarized below in Table A.

TABLE A

Stabilizing Effect of Sunflower Seed Oil
Compared with Other Vegetable Oils
(Storage temperature 23° C.)

| Time (days) | Cell Viability (CFU/cc on MRS Agar) | | |
|---|---|---|---|
| | Sunflowerseed | Cottonseed | Corn |
| 0 | $45 \times 10^7$ | $48 \times 10^7$ | $56 \times 10^7$ |
| 9 | $53 \times 10^7$ | $48 \times 10^7$ | $43 \times 10^7$ |
| 70 | $52 \times 10^7$ | $39 \times 10^7$ (19% loss) | $32 \times 10^7$ |
| 120 | $51 \times 10^7$ (negligible loss) | $34 \times 10^7$ (29% loss) | $10 \times 10^7$ (82% loss) |

Similar tests were made with soybean oil and canola oil. With the soybean oil, there was a loss of cell viability of 70–75% within 10 days. The canola oil showed better cell preservation, but after 120 days a cell loss of around 28% was observed. These results as well as the results of Table A indicate that sunflower seed oil has special properties for maximizing the preservation of Lactobacilli in oil suspension.

We claim:

1. A stabilized liquid bacterial composition for administration to animals, consisting essentially of anhydrous sunflower seed oil having dispersed therein dried viable cells of animal-probiotic Lactobacilli together with a sufficient amount of fumed silica to maintain said cells in anhydrous suspension, said suspension containing from $1 \times 10^8$ to $1 \times 10^{10}$ colony forming units (CFU) of said cells per cubic centimeter of the oil suspension, said cells having been prepared for addition to said oil by drying under conditions favorable to cell stability to a water activity ($a_w$) below 0.20.

2. The stabilized suspension of claim 1 in which said cells are *Lactobacillus acidophilus*.

3. The stabilized suspension of claim 1 in which said cells have a water activity ($a_w$) below 0.10.

4. The stabilized suspension of claim 1, in which said cells have been dried for addition to said oil in the presence of stabilizing organic compounds selected from the group consisting of (i) L-ascorbic acid or an edible water-soluble salt thereof, (ii) glutamic acid or edible water-soluble salts thereof, and (iii) mixtures of said compounds, said dried cells having a water activity ($a_w$) below 0.10.

* * * * *